United States Patent [19]

Starnes et al.

[11] Patent Number: 5,268,280
[45] Date of Patent: Dec. 7, 1993

[54] **METHOD FOR GLUCOSE ISOMERIZATION USING XYLOSE ISOMERASE PURIFIED FROM *THERMOTOGA MARITIMA* AND *THERMOTOGA NEAPOLITANA***

[75] Inventors: Robert L. Starnes, Sacramento, Calif.; Robert M. Kelly, Ellicott City; Stephen H. Brown, Owings Mills, both of Md.

[73] Assignees: Novo Nordisk A/S, Bagsvaerd, Denmark; The Johns Hopkins University, Baltimore, Md.

[21] Appl. No.: 47,591

[22] Filed: Apr. 13, 1993

Related U.S. Application Data

[62] Division of Ser. No. 600,544, Oct. 19, 1990, Pat. No. 5,219,751.

[51] Int. Cl.$^5$ .................. C12P 19/24; C12N 11/00; C12N 9/58
[52] U.S. Cl. .................. 435/94; 435/223; 435/174
[58] Field of Search .................. 435/223, 94, 174

[56] References Cited

U.S. PATENT DOCUMENTS

| 3,868,304 | 2/1975 | Messing | 435/234 |
|---|---|---|---|
| 3,941,655 | 3/1976 | Heady et al. | 435/234 |
| 4,593,001 | 6/1986 | Horwath | 435/94 |
| 4,687,742 | 8/1987 | Skoet et al. | 435/234 |
| 5,041,378 | 8/1991 | Drummond et al. | 435/234 |

FOREIGN PATENT DOCUMENTS

| 1004613 | 2/1977 | Canada. |
| 0194760 | 9/1986 | European Pat. Off.. |
| WO89/01520 | 2/1989 | PCT Int'l Appl.. |
| WO90/00196 | 1/1990 | PCT Int'l Appl.. |

*Primary Examiner*—David M. Naff
*Assistant Examiner*—Michael V. Meller
*Attorney, Agent, or Firm*—Steve T. Zelson; Elias J. Lambiris

[57] ABSTRACT

This invention is in the field of glucose isomerization enzymes. More specifically, the invention is directed to a novel xylose isomerase, a process for the preparation of this enzyme, the use of this enzyme in glucose isomerization processes, and glucose isomerization processes.

The enzyme is preferrably derived from *Thermotoga maritima* or *Thermotoga neapolitana*. The enzyme has a temperature optimum above 90° C., pH optimum in the range of from 6 to 7 and a residual activity at 90° C. of more than 40% after 30 minutes and/or residual activity at 98° C. of more than 20% after 30 minutes. The enzyme can also be in immobilized form.

10 Claims, 7 Drawing Sheets

METHOD FOR GLUCOSE ISOMERIZATION USING XYLOSE ISOMERASE PURIFIED FROM *THERMOTOGA MARITIMA* AND *THERMOTOGA NEAPOLITANA*

This is a divisional application of co-pending application Ser. No. 07/600,544, filed Oct. 19, 1990, now U.S. Pat. No. 5,219,751.

TECHNICAL FIELD

This invention is in the field of glucose isomerization enzymes. More specifically, the invention is directed to a novel xylose isomerase, a process for the preparation of this enzyme, the use of this enzyme in glucose isomerization processes, and glucose isomerization processes.

BACKGROUND ART

Glucose isomerization enzymes catalyze the conversion of glucose (dextrose) to fructose in the manufacture of High Fructose Syrup (HFS), i.e. a syrup containing a mixture of glucose and fructose. All described glucose isomerases fundamentally are xylose isomerases. Thus, for the sake of clarity, the enzyme of this invention ordinarily will be identified as xylose isomerase, although the most important application thereof is for the isomerization of glucose to fructose.

Due to the high sweetening power of fructose and the low tendency to crystallize HFS is widely used in industry, where it can replace liquid sucrose and invert syrup in many food and beverage products such as soft-drinks, baked goods, canned fruit, ice cream, confectionery, jams and jellies.

A large number of patents are directed to different microbial sources of xylose isomerase. Many bacteria, e.g. species belonging to the genera Streptomyces; Actinoplanes: Bacillus: and Flavobacterium, and fungi, e.g. species belonging to the class Bacidiomycetes, have been identified in the patent literature as xylose isomerase producing microorganisms, vide e.g. U.S. Pat. No. 4,687,742 and EP patent publication No. 352,474.

For many years the wish has existed to perform the isomerization process at elevated temperatures, vide e.g. U.S. Pat. Nos. 4,410,627; 4,411,996; and 4,567,142. The conversion of glucose to fructose is a temperature dependent equilibrium reaction: The higher the temperature, the higher the yield of fructose at equilibrium. However, the isomerization temperature strongly affects the enzyme activity and stability. Higher temperatures will result in higher enzyme activity (increased glucose conversion rate), but also increased thermal denaturation of the enzyme. Therefore, the stability, and hence the productivity, decreases with higher temperatures. On the other hand, lower isomerization temperatures will lead to increased risk of microbial infection. The infection risk is minimized when operating at temperatures of from approximately 60° C.

Of outstanding commercial interest are syrups containing approximately 55% (w/w dry substance) fructose. At this fructose level the syrup attains equal sweetness with sucrose on a weight to weight dry basis, and is used interchangeably as a total or partial replacement for sucrose in many food products, and especially in carbonated soft drinks.

Regards to thermal stability and enzyme consumption greatly influence the isomerization conditions. Thus, in practise, due to the life time of the enzyme and the productivity, syrups containing more than approximately 42% fructose are obtained by non-enzymatic treatment of the enzymatically manufactured HFS. The non-enzymatical treatment comprises expensive chromatographical separation to obtain a syrup with the desired fructose concentration. Therefore, an extensive search for xylose isomerases that allow the isomerization process to be carried out at higher temperatures in favour of a higher fructose yield has taken place.

It is an object of the invention to provide a xylose isomerase that in respect to thermal stability is superior over any hitherto known xylose isomerase. Moreover, it is an object of the invention to provide a isomerization process for high yield glucose conversion.

SUMMARY OF THE INVENTION

Now a novel xylose isomerase has been found that possesses outstanding glucose isomerization properties. Accordingly, in its first aspect, the present invention provides a xylose isomerase having a temperature optimum above 90° C.; pH optimum in the range of from pH 6 to 7; a residual activity after 30 minutes at 90° C. of more than 40%, or a residual activity after 30 minutes at 98° C. of more than 20%. In another aspect, the present invention provides a xylose isomerase having a temperature optimum above 90° C.; pH optimum in the range of from pH 6 to 7; a residual activity after 30 minutes at 90° C. of more than 40%, and a residual activity after 30 minutes at 98° C. of more than 20%; and having immunochemical properties identical or partially identical to those of the xylose isomerase derived from *Thermotoga maritima*, DSM No. 3109, or *Thermotoga neapolitana*. DSM No. 4359 or DSM No. 5068. In a more specific aspect of the present invention, there is provided a xylose isomerase obtainable from a xylose isomerase producing strain of *Thermotoga sp.*; preferably *T. maritima* or *T. neapolitana*. In a yet more specific aspect of the present invention, there is provided a xylose isomerase obtainable from *T. maritima*. DSM No. 3109, or *T. neapolitana*, DSM No. 4359 or DSM No. 5068, or a mutant or a variant thereof. In a preferred embodiment of the present invention, there is provided a xylose isomerase in the form of an immobilized enzyme.

In a third aspect of the invention, there is provided a process for the preparation of the enzyme, which process comprises cultivation of a xylose isomerase producing strain of *Thermotoga sp.* in a suitable nutrient medium, containing carbon and nitrogen sources and inorganic salts, followed by recovery of the desired enzyme. In a more specific aspect, a strain of *T. neapolitana* or *T. maritima* is cultivated. In a yet more specific aspect, *T. maritima*, DSM No. 3109, or *T. neapolitana*, DSM No. 4359 or DSM 5068, a mutant or a variant thereof, is cultivated.

In a fourth aspect of the invention, the use of a xylose isomerase of the invention in glucose isomerization processes is claimed. In a more specific aspect, there is provided a glucose isomerization process, in which a feed liquor, containing from about 20 to 65% (w/w dry substance) glucose, is reacted with a xylose isomerase of the invention at a temperature of from 50° to 130° C., at a pH of from 3.5 to 8, and a reaction time of from 10 seconds to about 5 hours. In another specific aspect, there is provided a two step glucose isomerization process, in which a feed liquor, containing from about 20 to 65% (w/w dry substance) glucose, in the first step is reacted with an isomerization enzyme at a temperature of from 50° to 80° C., at a pH of from 6 to 8, and a reaction time of from 10 minutes to about 5 hours, to produce a high fructose syrup, containing from about 40 to about 50% fructose, which high fructose syrup in the second step is reacted with an isomerization enzyme at a temperature of from 80° to 130° C., at a pH of from 3.5 to 8, and a reaction time of from 10 seconds to about 5 hours, to produce a high fructose syrup, containing from about 50 to about 60% fructose, the isomerization enzyme employed in the second step being a xylose isomerase of the invention. In a preferred embodiment, the isomerization enzyme employed in both steps is a xylose isomerase of the invention. In another preferred embodiment, the xylose isomerase is immobilized and retained in a fixed bed, through which the glucose or glucose/fructose solution flows.

BRIEF DESCRIPTION OF DRAWINGS

The present invention is further illustrated by reference to the accompanying drawings, in which.

DETAILED DISCLOSURE OF THE INVENTION

The enzyme

The enzyme of the invention is a novel xylose isomerase that catalyzes the conversion of D-glucose to D-fructose. The enzyme possesses thermostability superior to any known xylose isomerase. The extraordinary thermostability is demonstrated by comparison to an enzyme representative of the thermostability of the known xylose isomerases, namely a xylose isomerase obtained from *Streptomyces murinus* (vide U.S. Pat. No. 4,687,742 and EP patent publication No. 352,474). The xylose isomerase of the invention can be described by the following characteristics.

Physical-chemical properties

Figure 1:
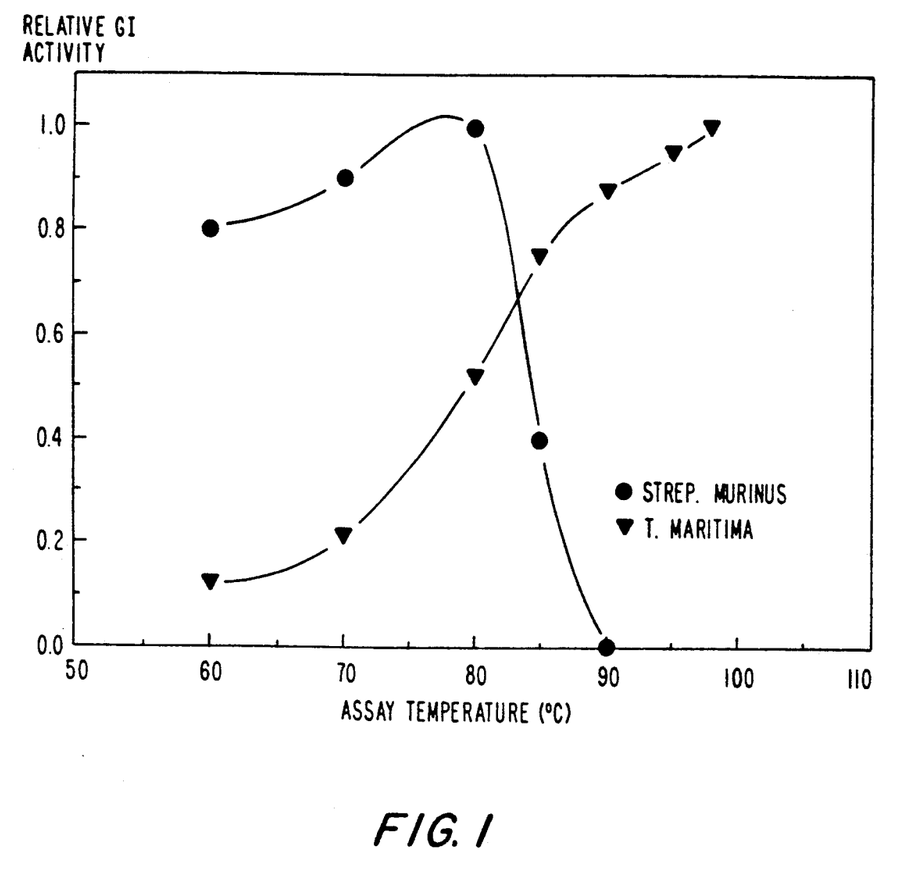
FIG. 1 shows the relation between temperature and activity of the enzyme of the invention.

As shown in FIG. 1, the xylose isomerase of the invention is active in a temperature range of from below 60° C. to above 98° C. The temperature optimum is at temperatures above 90° C., more precisely above 95° C.

Figure 2:
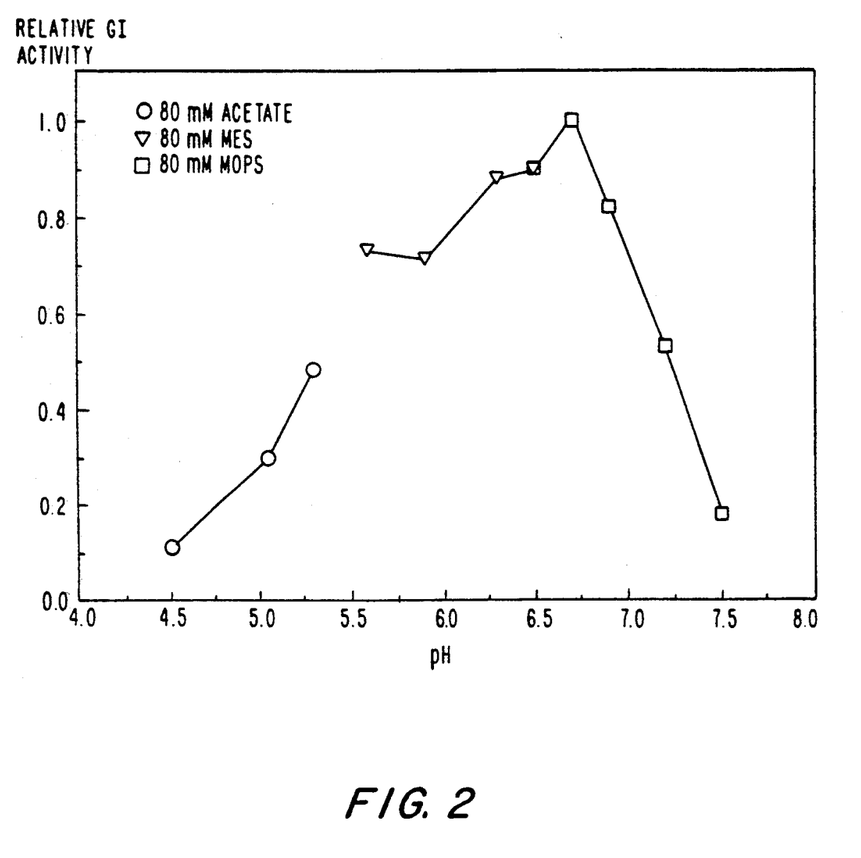
FIG. 2 shows the relation between pH and activity of the enzyme of the invention.

As shown in FIG. 2, the enzyme of the invention has pH optimum in the range of from pH 6 to 7.5, more precisely pH 6 to 7 (around pH 6.6), when measured in a MOPS (3-(N-morpholino)-propanesulphonic acid) buffer system (cf. Example 3).

Figure 3A:
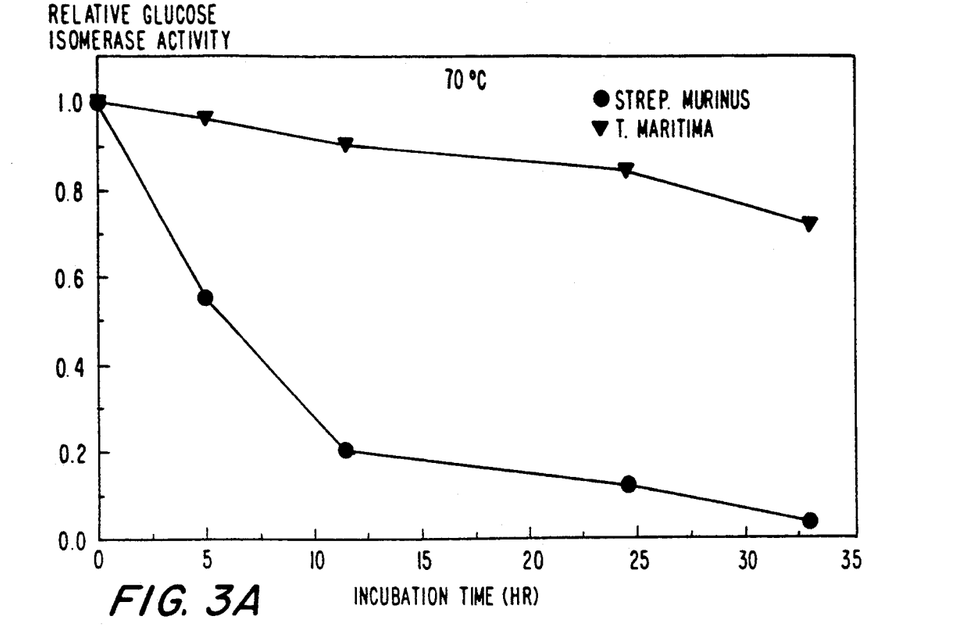
FIGS. 3-4 show a comparison of the residual activity (thermostability) of the enzyme of the invention and a known xylose isomerase at various temperatures (70°, 80°, 90° and 98° C.)
Figure 3B:
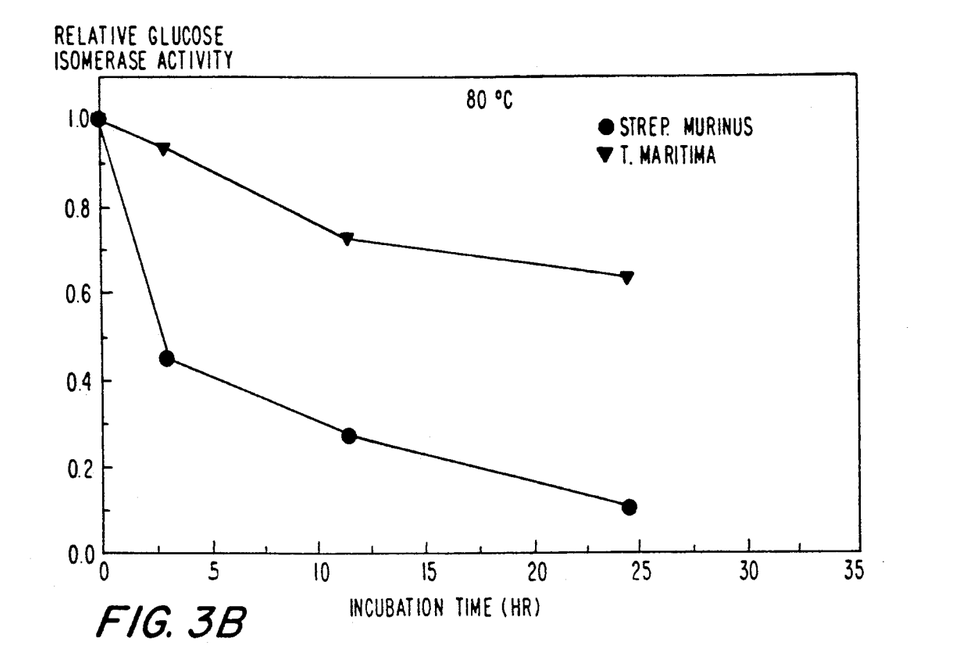
Figure 4A:
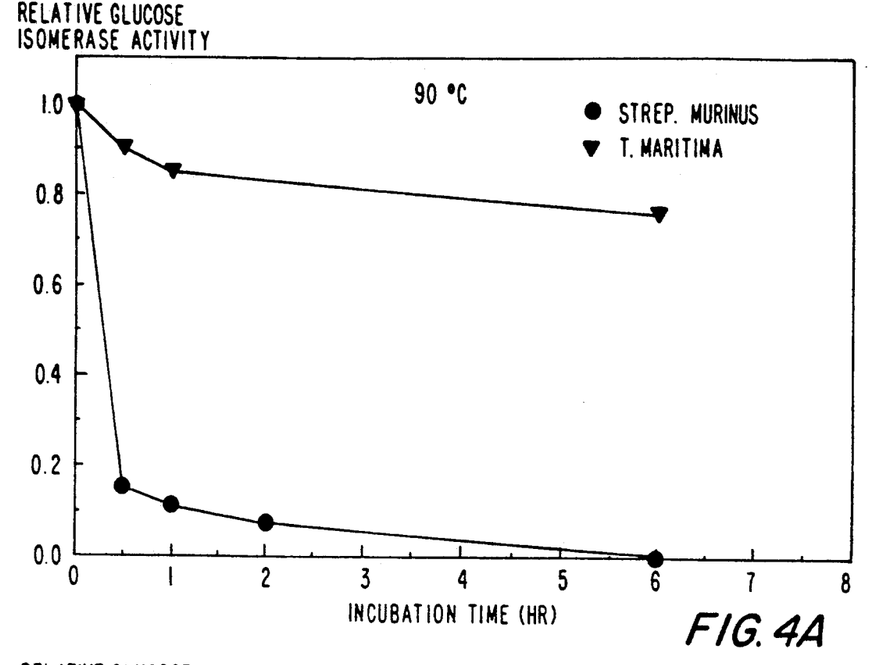
Figure 4B:
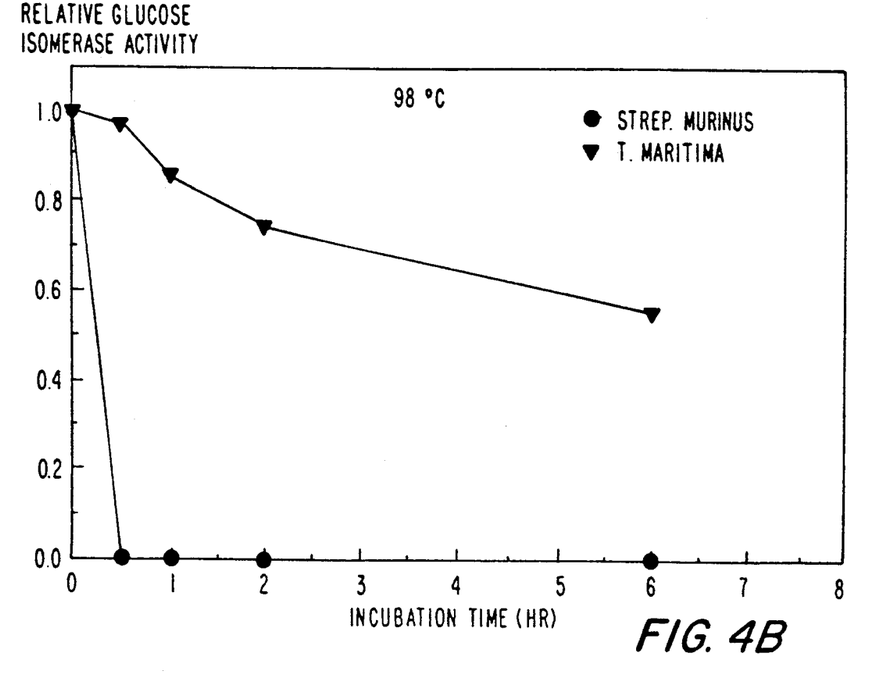

As shown in FIGS. 3-4, the thermostability of the enzyme of the invention, described as the residual activity, is:

At 70° C.: More than 60%, preferably more than 80%, after 5 hours; or more than 30%, preferably more than 50%, after 33 hours.

At 80° C.: More than 60%, preferably more than 80%, after 3 hours; or more than 30%, preferably more than 50%, after 24 hours.

At 90° C.: More than 40%, preferably more than 60%, more preferably more than 80%, after 30 minutes; or more than 20%, preferably more than 40%, more preferably more than 60%, after 6 hours.

At 98° C.: More than 20%, preferably more than 40%, more preferably more than 60%, yet more preferably more than 80%, after 30 minutes; or more than 20%, preferably more than 40%, after 6 hours.

Figure 5:
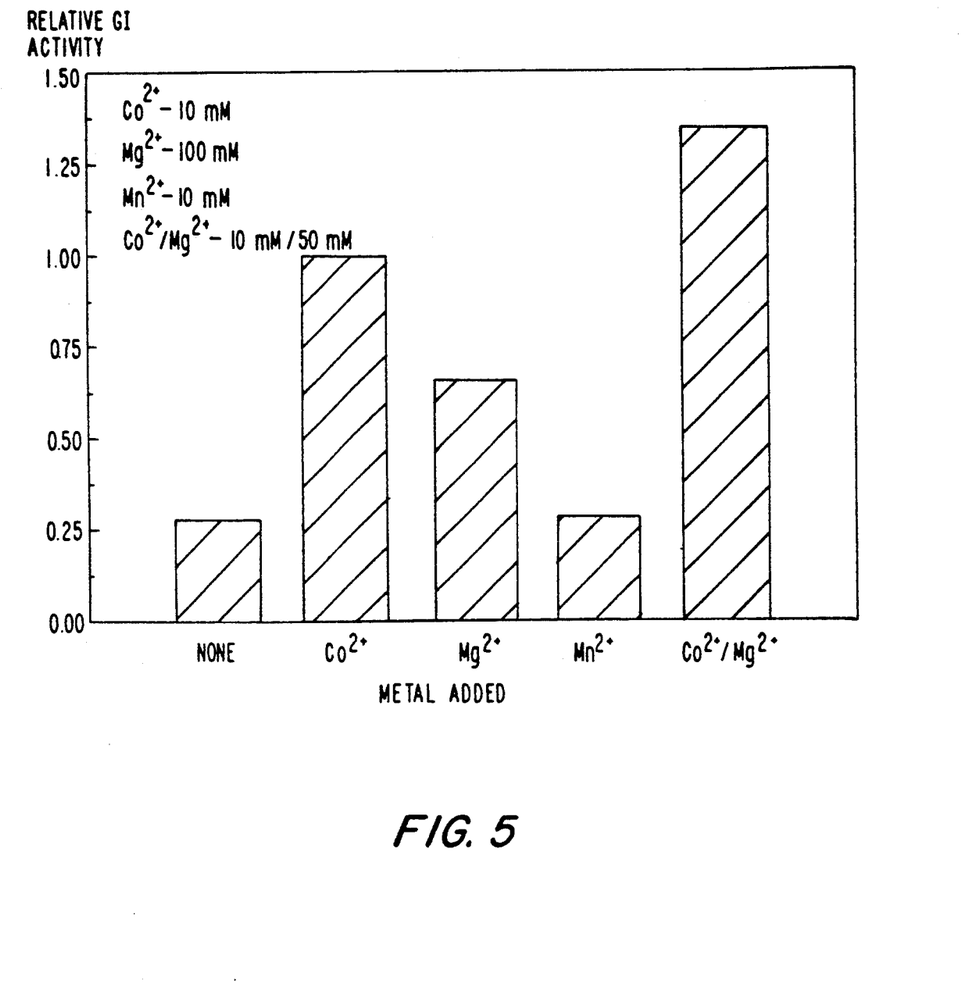
FIGS. 5-6 show the effect of divalent metal ions.
Figure 6:
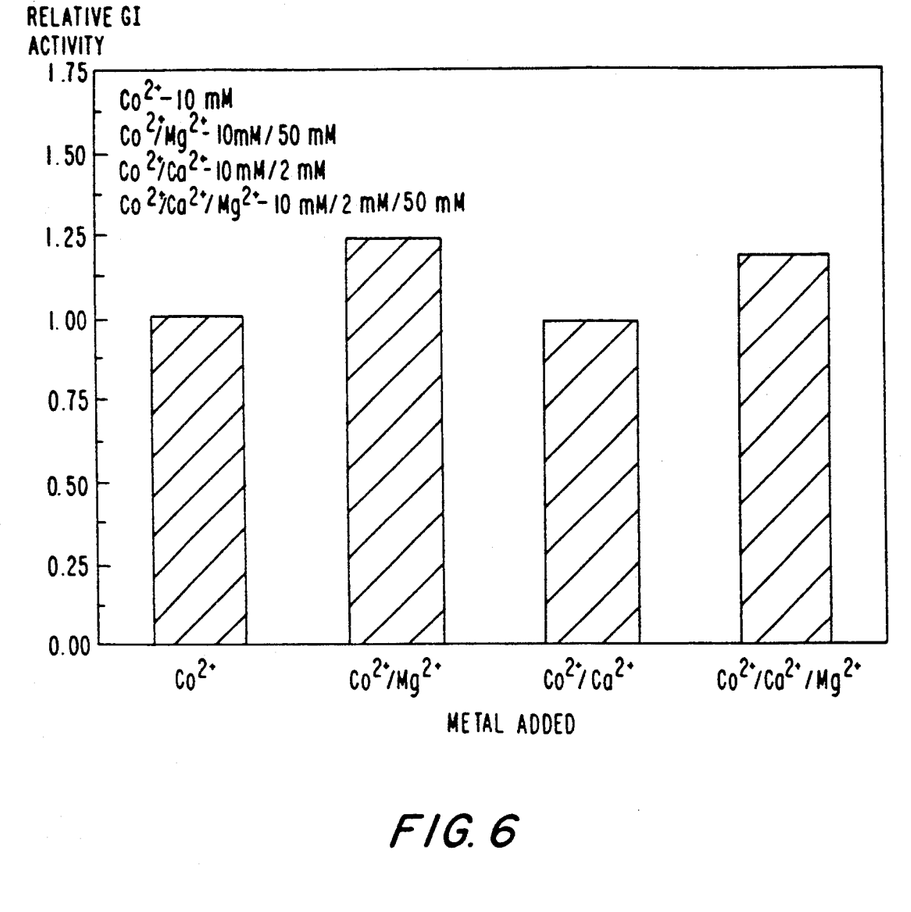

Investigations in relation to the effect of metal ions on the enzyme of the invention showed a stabilizing effect of $Co^{2+}$ and $Mg^{2+}$. This effect is illustrated in FIGS. 5-6.

Immunochemical properties

The immunochemical properties can be determinated immunologically by cross-reaction identity tests. The identity tests can be performed by the well-known Ouchterlony double immunodiffusion procedure or by tandem crossed immunoelectrophoresis according to N. H. Axelsen; Handbook of Immunoprecipitation-in-Gel Techniques; Blackwell Scientific Publications (1983), chapters 5 and 14. The terms "antigenic identity" and "partial antigenic identity" are described in the same book, chapters 5, 19 and 20.

Monospecific antiserum is generated, according to the above mentioned method, by immunizing rabbits with the purified xylose isomerase of the invention. The immunogen is mixed with Freund's adjuvant and injected subcutaneously into rabbits every second week. Antiserum is obtained after a total immunization period of 8 weeks, and immunoglobulin is prepared therefrom as described by N. H. Axelsen, supra.

Preparation of the enzyme

The enzyme is obtainable by cultivation of a xylose isomerase producing strain of *Thermotoga sp.* in a suitable nutrient medium, containing carbon and nitrogen sources and inorganic salts, followed by recovery and purification of the desired enzyme by conventional means. The enzyme can also be obtained by recombinant DNA-technology.

A process illustrating the preparation of the enzyme of the invention by fermentation is described in Example 1.

The microorganism

The enzyme of the invention is obtainable from thermophilic eubacteria belonging to the genus Thermotoga (Thermotogales).

The organisms belonging to the genus Thermotoga grow at temperatures of from 55° to 90° C., with growth optimum around 80° C. They are obligate anaerobes (somewhat $O_2$ tolerant). They are halotolerant, and grow optimally at 2.7% NaCl, with a range of 0.25 to 3.75% NaCl. They grow optimally at pH 6.5, with a pH range of 5.5 to 9. They are obligate heterotroph, show fermentative growth on a range of saccharides, including glucose, ribose, xylan, maltose, starch, etc. They can grow in presence or absence of $S^0$, and produce $H_2$ ($H_2S$), $CO_2$, acetate, lactate, and several other minor organic products.

Three strains of the genus Thermotoga are deposited: *T. maritima*, DSM No. 3109; and *T. neapolitana*, DSM No. 4359 and DSM No. 5068.

The isomerization process

By employing the enzyme of the invention in an isomerization process, the reaction temperature—and hence the yield of fructose—can be elevated, when compared to hitherto known isomerization processes. In a one step process of the invention the temperature should be in the range of from 50° to 130° C.

In another aspect of the invention, a two step isomerization process is carried out. In this process, the isomerization, in its first step, is carried out as a conventional isomerization process, employing either a conventional isomerization enzyme or a xylose isomerase of the invention, to produce a high fructose syrup containing from about 40 to 50% fructose. In the second step, the end product from the first step is subjected to isomerization at elevated temperatures, i.e. of from 80° to 130° C., and at a pH of from 3.5 to 8, by employing a xylose isomerase of the invention, to produce a high fructose syrup containing from about 50 to 60% fructose. The rationale behind this process being that the time necessary for the product to stay at elevated temperatures (the second process step) can be reduced considerably, when employing a starting product that is already a high fructose syrup.

Other isomerization conditions can be as for conventional isomerization processes.

The reaction time can be in the range of 10 seconds to 5 hours, depending on the isomerization temperature, specific activity of the enzyme preparation employed, etc.

The isomerization pH affects enzyme activity, stability and by-product formation. The isomerization pH should be in the range of from 3.5 to 8, more preferred 4.5 to 7. By-product formation due to glucose and fructose decomposition increases at higher pH levels.

The feed syrup dry substance content (DS) influences the rate of fructose formation. Too high a DS level results in lower apparent enzyme activity. On the other hand, too dilute a syrup will lead to a lower optimum substrate/enzyme ratio and increased risk of microbial infection. The feed liquor should contain of from 20 to 65%, more preferred 30 to 60% w/w dry substance glucose.

The concentration of monosaccharides in the feed syrup should be as high as possible in order to obtain the maximum isomerization rate. With a low monosaccharide concentration in the feed syrup the isomerization temperature must be elevated in order to attain a given fructose concentration.

For optimal performance of the isomerization process, the xylose isomerase of the invention can be immobilized. The isomerization process of the invention can then be carried out as a continuous, fixed-bed reactor process. In addition to the convenience of continuous operation, the fixed-bed process permits a short reaction time thereby minimizing by-product formation.

The enzyme can be immobilized by methods known in the art to produce xylose isomerase preparations with acceptable high unit activities.

The following examples further illustrate the present invention.

EXAMPLE 1

Preparation

*T. maritima*, DSM No. 3109, was grown anaerobically in a 50 l fermentor on a medium with the following composition:

| | |
|---|---|
| NaCl | 15.00 g/l |
| Na$_2$SO$_4$ | 2.00 g/l |
| KCl | 0.35 g/l |
| NaHCO$_3$ | 0.10 g/l |

-continued

| | |
|---|---|
| KBr | 0.05 g/l |
| H$_3$BO$_3$ | 0.02 g/l |
| MgCl$_2$; 6 H$_2$O | 5.40 g/l |
| CaCl$_2$; 2 H$_2$O | 0.75 g/l |
| SrCl$_2$; 6 H$_2$O | 0.01 g/l |
| Tryptone (Difco) | 3.0 g/l |
| Yeast Extract (Difco) | 1.0 g/l |
| Xylose (Sigma X1500) | 5.0 g/l |

Figure 7:
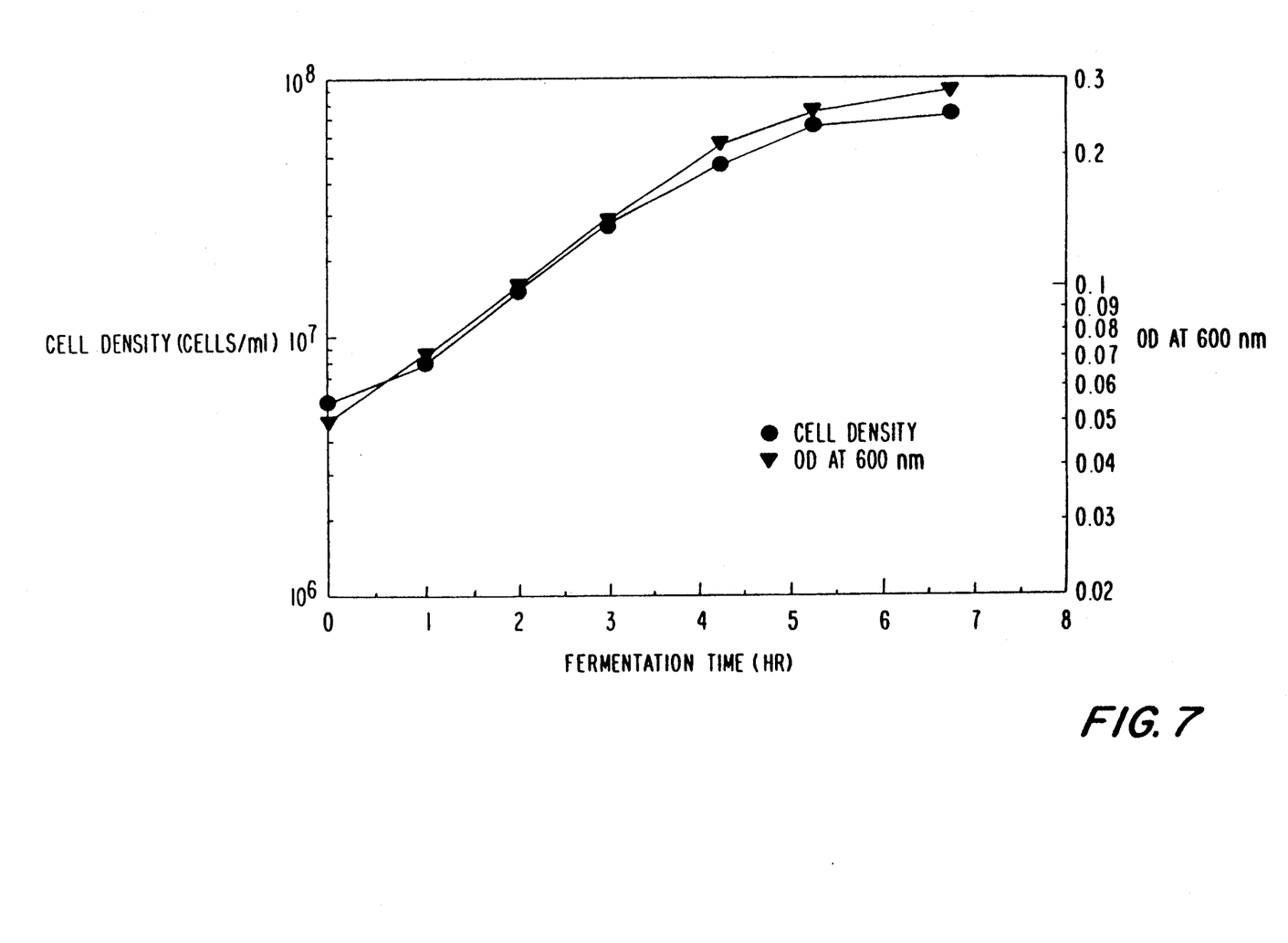
FIG. 7 shows the relation between cell density (cells/ml) and $OD_{600}$, respectively, and the fermentation time (hours).

Xylose was sterilized separately. pH was adjusted to 6.0–6.5 with H$_2$SO$_4$ at room temperature. Na$_2$S; 9 H$_2$O (0.5 g/l) was added before inoculation. The fermentation was run at 80° C., 100 rpm, with an N$_2$ sparge of about 0.05 vvm. An 8% inoculum was used (on the same media), and the run lasted about 8 hours, to an OD$_{600}$ of about 0.3. In FIG. 7 the relation between cell density and optical density at 600 nM (OD$_{600}$), respectively, and the fermentation time is shown.

Cells were harvested using a Sharples centrifuge, and frozen until sonification. The cell yield was 25 g wet weight.

Cell extracts were prepared by sonicating a cell suspension in a Tekmar sonicator for 6×30 seconds at 50% duty cycle. Membranes and cell debris were removed by centrifugation at 25,000×g for 30 minutes. The extract was dialyzed overnight against 50 mM MOPS buffer, pH 7.0, containing 0.02% sodium azide, and stored at 4° C.

EXAMPLE 2

Analytical method

Assay for xylose isomerase activity was performed the following way: 50–200 μl cell extract, obtained as described in Example 1, were added to 2.5 ml of a mixture containing 1M fructose; 80 mM MOPS, pH 6.9; and 10 mM Co$^{2+}$. The mixture was incubated at 80° C. for 60 minutes, and glucose was determined by a standard glucose oxidase type assay (Sigma 510).

EXAMPLE 3

Characterization

Temperature optimum: 50–200 μl cell extract, obtained as described in example 1, were added to 2.5 ml of a mixture containing 1M fructose; 80 mM MOPS, pH 6.9; and 10 mM Co$^{2+}$. Several such mixtures were incubated for 60 minutes at various temperatures in the range of from 60° C. to 98° C. The result is shown in FIG. 1.

pH optimum: 50–200 μl cell extract, obtained as described in example 1, were added to 2.5 ml of a mixture containing 1M fructose and 10 mM Co$^{2+}$, in each of the following buffer systems (pH values indicated on the figure):

80 mM acetate
80 mM MES;
80 mM MOPS; and
80 mM phosphate.

Each mixture was incubated for 60 minutes at 80° C., and assayed for glucose. The result is shown in FIG. 2.

Thermostability: The thermostability of the xylose isomerase obtained from *T. maritima* was compared to the known thermostable xylose isomerase obtained from *Streptomyces murinus*, by the following methods.

Xylose isomerase of the invention: 50–200 μl cell extract, obtained as described in Example 1, were added to 2.5 ml of a mixture containing 1M fructose; 80 mM MOPS, pH 6.9; and 10 mM $Co^{2+}$. Several such mixtures were incubated for 60 minutes at temperatures of 70°, 80°, 90° and 98° C., respectively. Samples were taken out at various incubation times and assayed for glucose.

Xylose isomerase obtained from *S. murinus*: Purified xylose isomerase, prepared according to U.S. Pat. No. 4,687,742, was diluted with 50 mM MOPS buffer, pH 7.5, to a dry substance content of 4%. 50-200 μl enzyme solution were added to 2.5 ml of a mixture containing 1M fructose; 80 mM MOPS, pH 7.5; and 10 mM $Co^{2+}$. Several mixtures were incubated for 30 minutes at temperatures of 70°, 80°, 90° and 98° C., respectively. Samples were taken out at various incubation times and assayed for glucose. The results are shown in FIGS. 3-4.

Effect of divalent metal ions: 50-200 μl cell extract, obtained as described in example 1, were added to 2.5 ml of a mixture containing 1M fructose; 80 mM MOPS, pH 6.9; and one or more of the following metal ions in the concentration cited:

$Co^{2+}$, 10 mM;
$Mg^{2+}$, 100 mM;
$Mn^{2+}$, 10 mM;
$Co^{2+}/Mg^{2+}$, 10 mM/50 mM;
$Co^{2+}/Ca^{2+}$, 10 mM/2 mM; and
$Co^{2+}/Ca^{2+}/Mg^{2+}$, 10 mM/2 mM/50 mM.

The mixtures were incubated for 60 minutes at 80° C., and assayed for glucose. The results are shown in FIGS. 5-6.

We claim:

1. A glucose isomerization process, comprising reacting a feed liquor containing about 20 to 65% (w/w dry substance) glucose with a substantially purified xylose isomerase which is derived from *Thermotoga maritima* or *Thermotoga neapolitana* at a temperature of from 50° to 130° C., a pH of from 3.5 and 8 and a reaction time of from 10 seconds to about 5 hours, wherein the xylose isomerase has the following properties:
   (a) temperature optimum above 90° C.;
   (b) pH optimum in the range of from 6 to 7; and
   (c) a residual activity at 90° C. of more than 40% after 30 minutes and/or a residual activity at 98° C. of more than 20% after 30 minutes.

2. The glucose isomerization process according to claim 1, wherein the xylose isomerase has immunochemical properties identical or partially identical to those of the xylose isomerase derived from *Thermotoga maritima* DSM No. 3109 or *Thermotoga neapolitana*, DSM No. 4359.

3. The glucose isomerization process according to claim 2, wherein the xylose isomerase is derived from *T. maritima* DSM No. 3109 or a mutant thereof.

4. The glucose isomerization process according to claim 2, wherein the xylose isomerase is derived from *T. neapolitana* DSM No. 4359 or a mutant thereof.

5. The glucose isomerization process according to claim 1, wherein the xylose isomerase is in the form of an immobilized enzyme.

6. A glucose isomerization process, comprising
   (a) reacting a feed liquor containing about 20 to 65% (w/w dry substance) glucose with a substantially purified xylose isomerase which is derived from *Thermotoga maritima* or *Thermotoga neapolitana* at a temperature of from 50° to 80° C., a pH of from 6 and 8 and a reaction time of from 10 minutes to about 5 hours, to produce a high fructose syrup containing from about 40 to about 50% fructose; and
   (b) reacting the high fructose syrup with the substantially purified xylose isomerase at a temperature of from 80° to 130° C., a pH of from 3.5 to 8 and a reaction time of from 10 seconds to about 5 hours to produce another high fructose syrup containing from about 50 to 60% fructose, wherein the xylose isomerase has the following properties:
   (a) temperature optimum above 90° C.;
   (b) pH optimum in the range of from 6 to 7; and
   (c) a residual activity at 90° C. of more than 40% after 30 minutes and/or a residual activity at 98° C. of more than 20% after 30 minutes.

7. The glucose isomerization process according to claim 6, wherein the xylose isomerase has immunochemical properties identical or partially identical to those of the xylose isomerase derived from *Thermotoga maritima* DSM No. 3109, or *Thermotoga neapolitana*, DSM No. 4359.

8. The glucose isomerization process according to claim 7, wherein the xylose isomerase is derived from *T. maritima* DSM No. 3109 or a mutant thereof.

9. The glucose isomerization process according to claim 7, wherein the xylose isomerase is derived from *T. neapolitana* DSM No. 4359 or a mutant thereof.

10. The glucose isomerization process according to claim 6, wherein the xylose isomerase is in the form of an immobilized enzyme.

* * * * *